US008608771B2

(12) United States Patent
Welch (10) Patent No.: US 8,608,771 B2
(45) Date of Patent: Dec. 17, 2013

(54) VASCULAR OCCLUSION DEVICE WITH ENHANCED FEEDBACK

(75) Inventor: Jonathan B. Welch, Greencastle, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 13/525,540

(22) Filed: Jun. 18, 2012

(65) Prior Publication Data

US 2013/0018407 A1 Jan. 17, 2013

Related U.S. Application Data

(60) Provisional application No. 61/507,354, filed on Jul. 13, 2011.

(51) Int. Cl.
*A61M 29/00* (2006.01)

(52) U.S. Cl.
USPC ........................................................ 606/194

(58) Field of Classification Search
USPC .................. 606/159, 191, 194, 198, 200; 604/96.01, 97.03, 100.01, 104, 105, 604/118, 506–509
See application file for complete search history.

(56) References Cited

U.S. PATENT DOCUMENTS

| 4,714,460 A | 12/1987 | Calderon |
| 4,883,459 A | 11/1989 | Calderon |
| 4,983,166 A | 1/1991 | Yamawaki |
| 5,072,739 A | 12/1991 | John |
| 6,306,124 B1 | 10/2001 | Jones et al. |
| 2005/0101989 A1 | 5/2005 | Cully et al. |
| 2007/0239197 A1* | 10/2007 | Dubey et al. ............... 606/193 |
| 2008/0058860 A1 | 3/2008 | Demond et al. |
| 2008/0097402 A1 | 4/2008 | Hoganson et al. |
| 2009/0264755 A1 | 10/2009 | Chen et al. |
| 2009/0318948 A1 | 12/2009 | Linder et al. |
| 2011/0137399 A1* | 6/2011 | Chomas et al. ............ 623/1.12 |

* cited by examiner

*Primary Examiner* — Ryan Severson
*Assistant Examiner* — Katherine M Shi
(74) *Attorney, Agent, or Firm* — Brinks Gilson & Lione (57) ABSTRACT

A vascular occlusion device for occluding a body cavity includes an elongate member, a deflecting device and an indicator device. The elongate member includes a proximal end and a distal end. An embolization material is injected into the body cavity through the distal end. The deflecting device is disposed at the distal end of the elongate member and configured to be deflected by the embolization material. The indicator device is disposed at the proximal end of the elongate member. The indicator device indicates a status of occlusion of the body cavity based on deflection of the deflecting device by the embolization material.

13 Claims, 11 Drawing Sheets

VASCULAR OCCLUSION DEVICE WITH ENHANCED FEEDBACK

CROSS-REFERENCE TO RELATED APPLICATIONS

This application claims the benefit of U.S. Provisional Application No. 61/507,354, filed on Jul. 13, 2011, entitled "VACSULAR OCCLUSION DEVICE WITH ENHANCED FEEDBACK," the entire contents of which are incorporated herein by reference.

FIELD

The present invention generally relates to medical devices, and more particularly to vascular occlusion devices.

BACKGROUND

A number of different devices may be used to occlude a body cavity including, for example, a blood vessel. An example of an occlusion device includes embolization coils. Embolization coils are permanent and promote blood clots or tissue growth over a period of time, thereby occluding the body cavity. However, while the blood clots or the tissue grows, blood may continue to flow past the coil and through the body cavity. It may take a significant period of time for sufficient tissue to grow to fully occlude the body cavity. This leaves a patient open to a risk of injury from the condition which requires the body cavity to be occluded. An example of such a condition includes, but is not limited to, an atrial septal defect such as a patent foramen ovale.

When it is desirable to quickly occlude a blood vessel, embolization material may be injected into the blood vessel. An external blood pressure monitoring means is generally used to determine the condition of embolization.

SUMMARY

The present disclosure provides an embolization kit that provides a visual or tactile indication of condition of embolization without using an external blood pressure monitoring means.

In one form, a vascular occlusion device for occluding a body cavity includes an elongate member, a deflecting device, and an indicator device. The elongate member includes a proximal end and a distal end. An embolization material is injected into the body cavity through the distal end. The deflecting device is disposed at the distal end of the elongate member and configured to be deflected by the embolization material. The indicator device is disposed at the proximal end of the elongate member. The indicator device indicates a status of occlusion of the body cavity based on deflection of the deflecting device by the embolization material.

In another form, a method of occluding a body cavity includes: positioning a distal end of a vascular occlusion device at a target site; expanding a deflecting device provided at the distal end of the occlusion device, wherein the deflecting device is configured to be deflected by an embolization material when the embolization overflows; injecting the embolization material into the body cavity; and determining a status of occlusion of the body cavity based on deflection of the deflecting device.

Further features and advantages of the invention will become readily apparent from the following description and from the claims.

DETAILED DESCRIPTION

Figure 1:
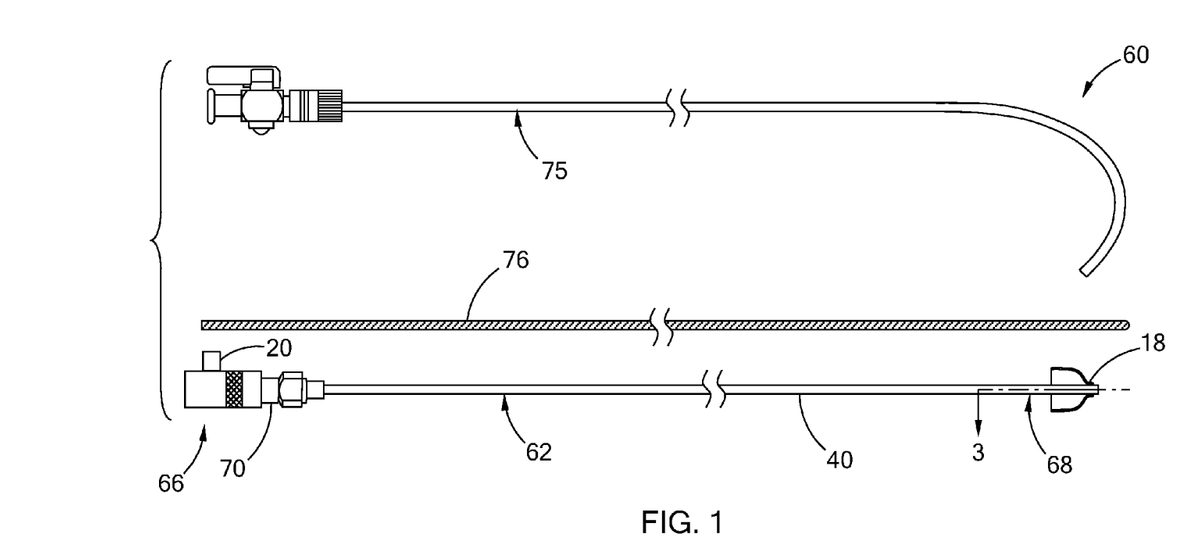
FIG. 1 is an exploded view of an embolization kit with a vascular occlusion device in accordance with the teachings of the present disclosure.
Figure 2:
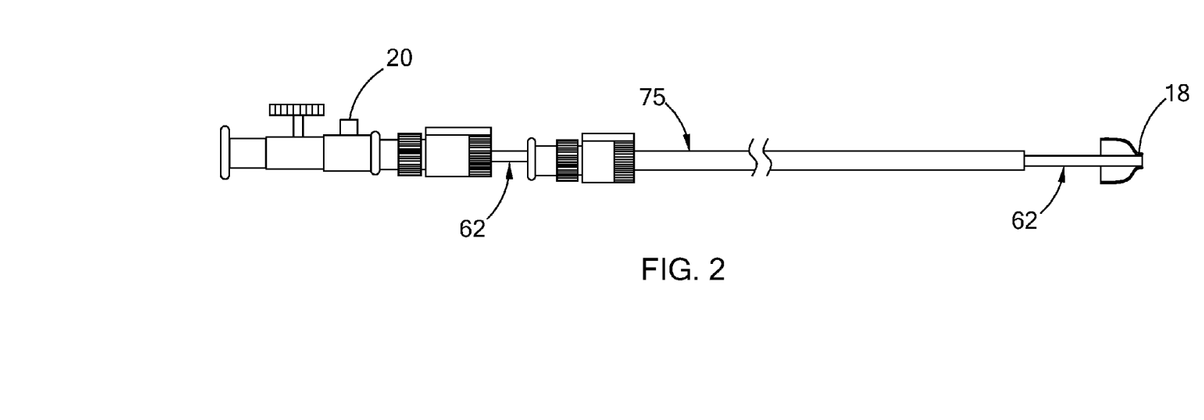
FIG. 2 is a side view of an embolization kit with a vascular occlusion device in accordance with the teachings of the present disclosure.

Referring now to FIGS. 1 to 2, an embolization kit 60 according to the principles of the present disclosure includes a vascular occlusion device 62, a guide catheter 75, and a guide wire 76. The guide catheter 75 allows the vascular occlusion device 62 to be inserted therethrough and provides stability of the vascular occlusion device 62 at a desired location within a body vessel. For example, the guide catheter 75 may stay stationary within a common visceral artery, e.g., a common hepatic artery, adding stability to the vascular occlusion device 62 as the vascular occlusion device 62 is advanced through the guide catheter 75 to a point of occlusion in a connecting artery, e.g., the left or right hepatic artery. In one embodiment, the guide catheter 75 is a polytetrafluoroethylene (PTFE) guide catheter or sheath for percutaneously introducing the vascular occlusion device 62 into a body vessel. Any suitable material may be used without falling beyond the scope or spirit of the present disclosure. The guide catheter 75 may have a size of about 4-8 french. The guide wire 76 provides the guide catheter 75 a path during insertion of the guide catheter 75 within the body vessel. The size of the guide wire 76 is based on the inside diameter of the guide catheter 75.

The vascular occlusion device 62 includes an elongate member 40 defining a proximal end 66 and a distal end 68, and an adaptor or hub 70 provided at the proximal end 66. The vascular occlusion device 62 further includes a deflecting device 18 provided at the distal end 68, an indicator device 20 provided at the proximal end 66, and a connecting member 24 (shown in FIGS. 3 and 4) connecting the indicator device 20 to the deflecting device 18. The vascular occlusion device 62 may be a microcatheter defining a lumen and is preferably made of a soft, flexible material such as silicone or any other suitable material.

Figure 3:
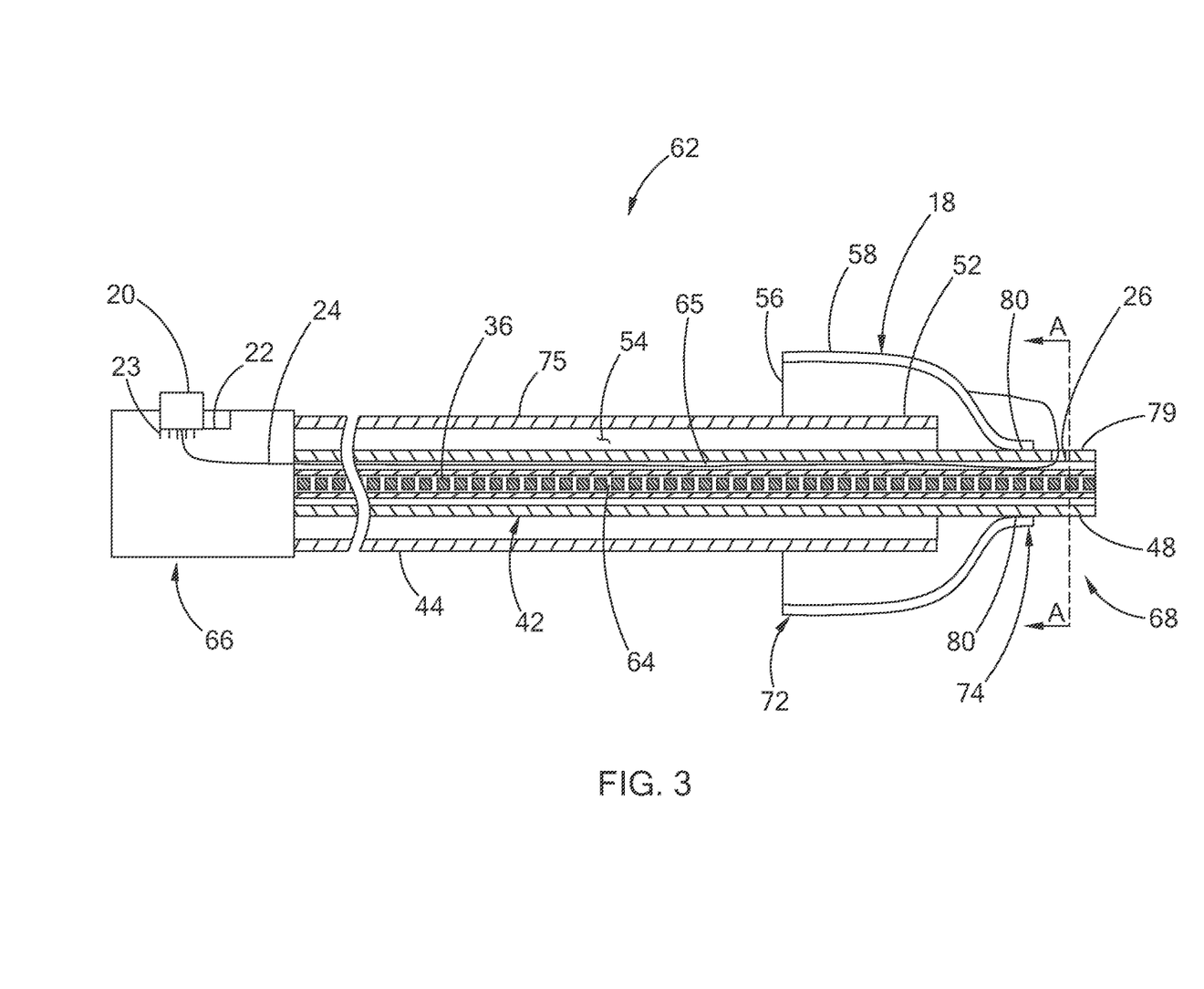
FIG. 3 is a partial, side view of a vascular occlusion device in accordance with a first embodiment of the present disclosure.
Figure 4:
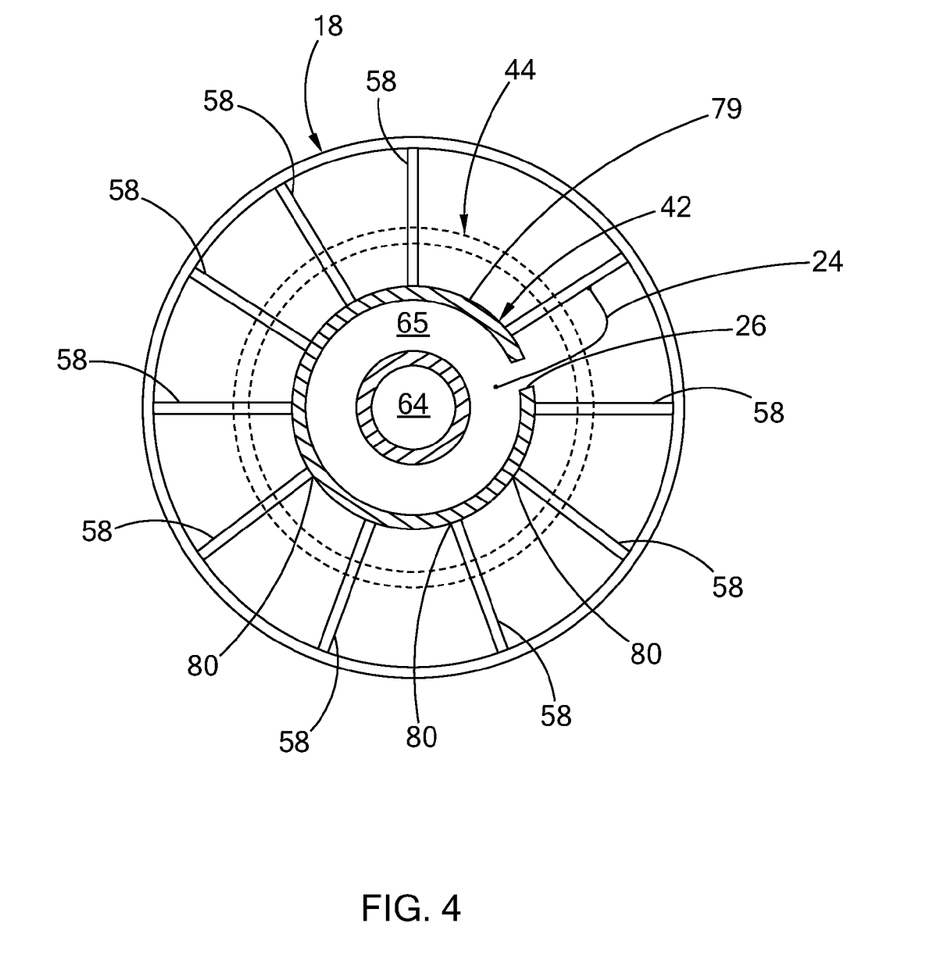
FIG. 4 is a cross-sectional view of the vascular occlusion device of FIG. 3, taken along line A-A.

Referring to FIGS. 3 and 4, the deflecting device 18 is pivotably attached to the distal end 68 of the elongate member 40 of the vascular occlusion device 62. The indicator device 20 is slidably disposed in a rail 22 at the proximal end 66 of the elongate member 40. The rail 22 has indicia 23 indicating the position or movement of the indicator device 20. The connecting member 24 may be in the form of a pull wire, a cord or a thread, or other forms that can pull the indicator device 20 to move in the rail 22 upon application of a tensile force. The elongate member 40 further includes an inner tubular member 42, and an outer tubular member 44 coaxially disposed around the inner tubular member 42 to define a deployment lumen 54 therebetween. The deflecting device 18 may be collapsed and received in the deployment lumen 54 when the vascular occlusion device 62 is guided into the body cavity.

The inner tubular member 42 has a distal end 48 protruding distally from the distal end 52 of the outer tubular member 44. The deflecting device 18 is pivotably attached to the distal end 48 of the inner tubular member 42. The inner tubular member 42 further defines an occlusion lumen 64 and a communication lumen 65. An embolization material 36 may be injected into the body cavity through the occlusion lumen 64. The distal end 48 of the inner tubular member 64 defines a radial opening 26 open to the communication lumen 65. The connecting member 24 extends in the communication lumen 65 and passes through the radial opening 26 to connect the deflecting device 18 outside the inner tubular member 64.

Figure 5:
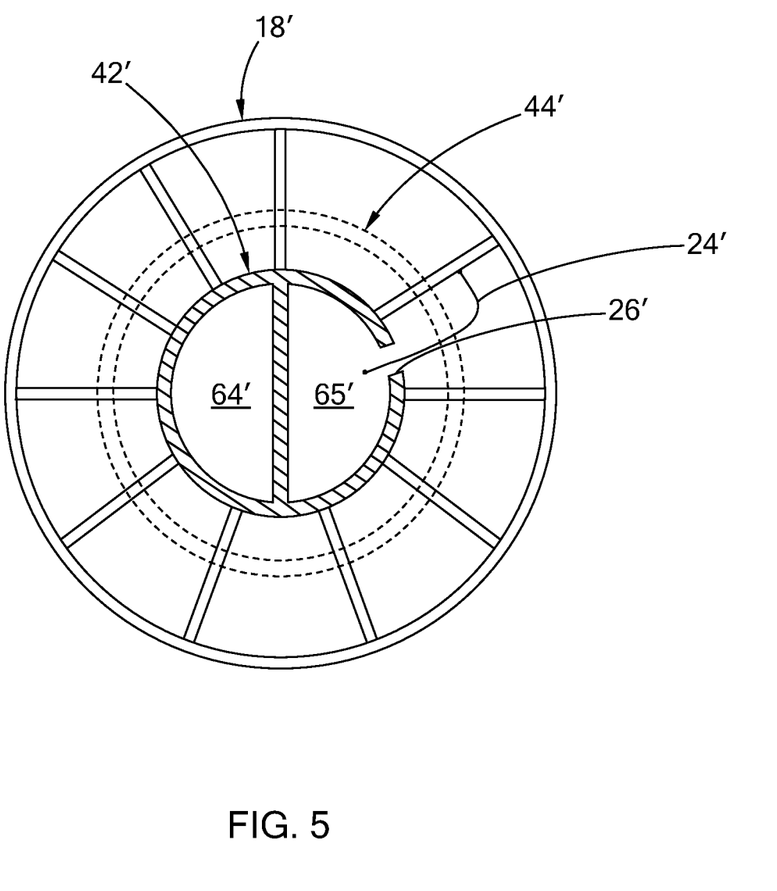
FIG. 5 is a cross-sectional view of an alternate form of a vascular occlusion device in accordance with the teachings of the present disclosure.

While the communication lumen 65 and the occlusion lumen 64 are shown in FIGS. 3 and 4 to be arranged in a coaxial manner, the communication lumen 65 and the occlusion lumen 64 may be arranged differently without departing from the scope of the present disclosure. For example, referring to FIG. 5, the inner tubular member 42' may define an occlusion lumen 64' and a communication lumen 65' arranged in a side-by-side relationship and a radial opening 26' is formed through the inner tubular member 42' adjacent to the communication lumen 65. Therefore, the connecting member 24' disposed in the communication lumen 65' of the inner tubular member 42' can extend through the cylindrical wall of the inner tubular member 42' to connect to the deflecting device 18' outside the inner tubular member 42'.

Referring back to FIGS. 3 and 4, the deflecting device 18 may be in the form of a covered stent and includes a frame having a plurality of struts 58 and a tubular portion 56 covering the openings between adjacent struts 58. The plurality of struts 58 are pivotably attached to the distal end 48 of the inner tubular member 42. The tubular portion 56 is attached to the plurality of struts 58. The plurality of struts 58 may be made of nitinol and are self-expandable upon deployment into the body cavity. The tubular portion 56 may be an expandable flap made of an impermeable or semi-permeable material, such as graft materials. The tubular portion 56 covers the plurality of struts 58 and prevents the embolization material 36 and the blood from flowing proximally through the deflecting device 18.

The plurality of struts 58 each define a proximal end 72 and a distal end 74. The distal ends 74 are pivotably attached to an outside surface 79 of the distal end 48 of the inner tubular member 42 to form hinge points 80. The proximal ends 74 of the struts 58 are pivotable about the hinge points 80. When the deflecting device 18 is in the expanded state, the proximal ends 72 of the struts 58 contact the interior walls 102 of the body vessel 100 (FIG. 6) to maintain the vascular occlusion device 62 in place.

When the distal end 68 of the vascular occlusion device 62 is at a point of occlusion in the body vessel 100, the embolization particles 36 may be loaded at the proximal end 66 via the hub 70 of the vascular occlusion device 62. In one example, saline solution is mixed with the embolization particles to form a slurry which is injected into the hub 70 of the vascular occlusion device 62 and advanced through the occlusion lumen 64. Alternatively and as illustrated in FIG. 3, the embolization particles may be pre-loaded within the occlusion lumen 64 of the vascular occlusion device 62. Saline solution or other suitable transferring fluid is introduced into the lumen 64 at the proximal end 66 of the vascular occlusion device 62 to advance the embolization particles to the distal end 68 of the vascular occlusion device 62.

Alternatively, a push wire (not shown) may be used to mechanically advance or push the embolization particles 36 through the vascular occlusion device 62. The size of the push wire depends on the diameter of the vascular occlusion device 62.

Figure 6:
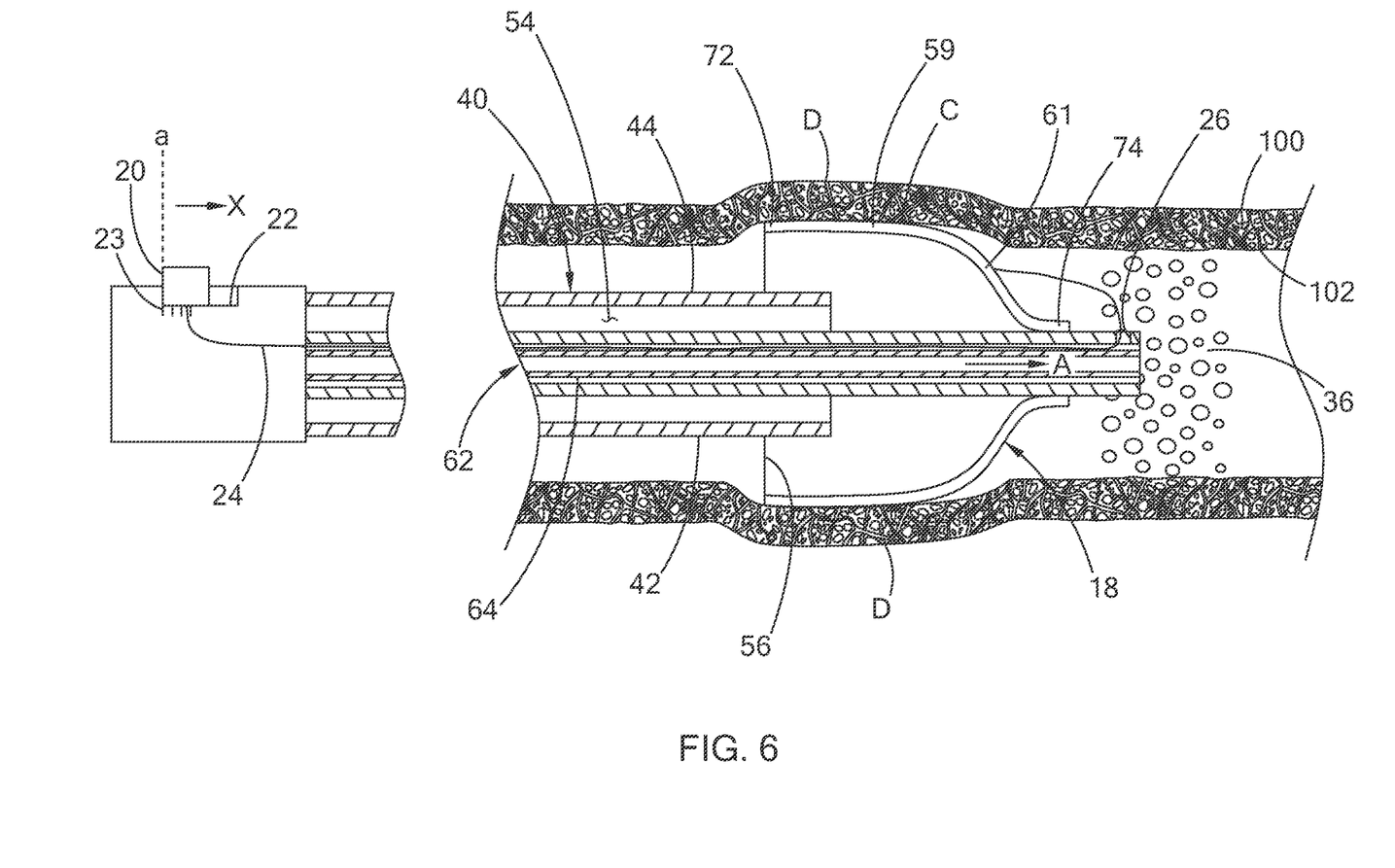
FIG. 6 is a partial, schematic environmental view of the vascular occlusion device of FIG. 3 in a blood vessel, wherein the deflecting device is in an expanded state.

Referring to FIG. 6, when the vascular occlusion device 62 is positioned at the target site, the deflecting device 18 is deployed in a body vessel 100 or a body cavity from the deployment lumen 54. The plurality of struts 58 are expanded radially so that the proximal ends 72 of the struts 56 contact the interior wall 102 of the body vessel 100 to help maintain the vascular occlusion device 62 at the target site. The tubular portion 56 is also expanded due to the radial expansion of the struts 58. In the expanded state, the deflecting device 18 has a configuration similar to an umbrella and defines a shape including a parallel tubular portion 59 adjacent the proximal ends 72 and a tapered portion 61 adjacent to the distal ends 74. The parallel tubular portion 59 of the deflecting device 18 contact the interior wall 102 of the body vessel 100 to define a contact area C between the deflecting device 18 and the interior wall 102 of the body vessel 100. The body vessel wall is bulged by the deflecting device 18 to form a bulging area D. When the deflecting device 18 is fully self-expanded, the indicator device 20 is at a first position (a).

After the deflecting device 18 is self-expanded, the embolization material 36 or solution is injected into the body vessel 100 through the occlusion lumen 64 of the inner tubular member 42 in a first direction A to occlude the target site. The deflecting device 18 in the expanded state blocks backflow of the blood or the embolization material 36. The indicator device 20 remains at the first position (a).

Figure 7:
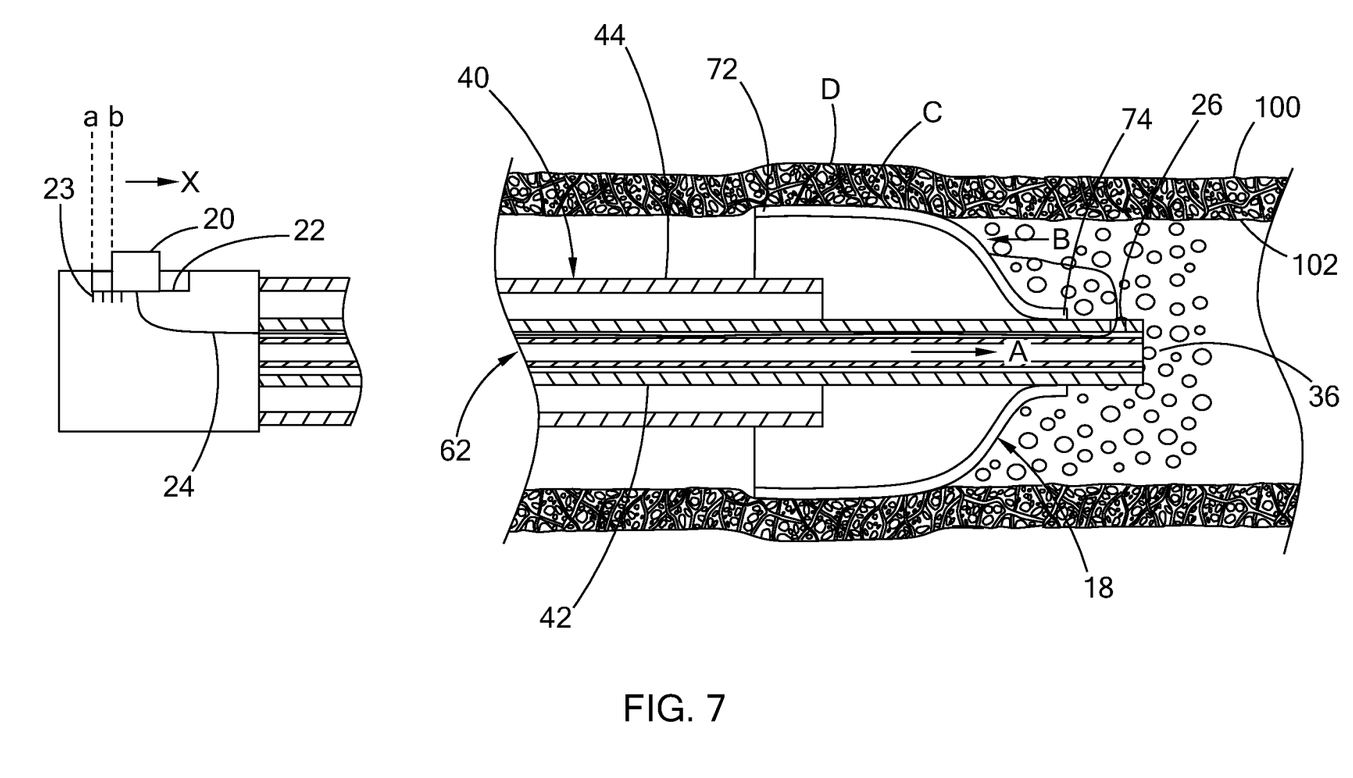
FIG. 7 is a partial, schematic environmental view of the vascular occlusion device of FIG. 6, wherein an embolization material starts to deflect the deflecting device.

Referring to FIG. 7, as more embolization material 36 is injected into the body vessel 100, the injection pressure increases. When the body vessel 100 becomes occluded, the embolization material 36 starts to flow in a second direction B opposite to the first direction A and starts to push and deflect the deflecting device 18. When the deflecting device 18 is deflected, the deflecting device 18 pulls the connecting member 24, which in turn pulls the indicator device 22 to move distally along direction X. As a result, the indicator device 20 is moved to a second position (b).

Figure 8:
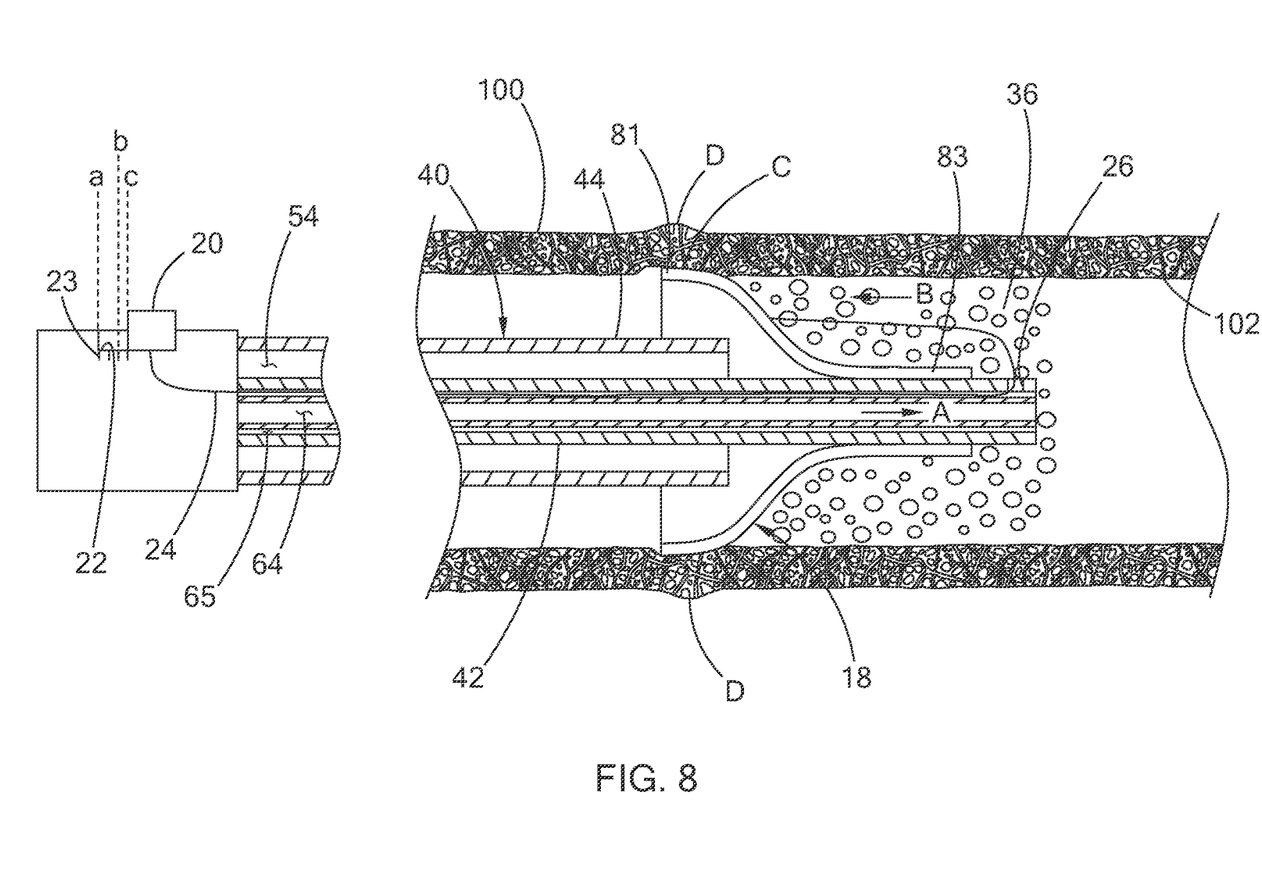
FIG. 8 is a partial, schematic environmental view of the vascular occlusion device of FIG. 6, wherein an embolization material deflects the deflecting device into a funnel shape.

Referring to FIG. 8, as more embolization material 36 continues to flow in the second direction B, the embolization material 36 pushes and deflects the deflecting device 18 into a funnel shape having a wide portion 81 adjacent the proximal ends 72 and a narrow portion 83 adjacent to the distal ends 74. The proximal ends 72 of the struts 53 are flared away from the distal ends of the struts 53. The contact area C between the expandable wall and the interior wall 102 of the body vessel 100 is reduced, so does the bulging area D of the body vessel.

When the deflecting device 18 is deflected into a funnel shape, a portion of the connecting member 24 is pulled outside the inner tubular member 42, causing the indicator device 20 to continue to move distally from the second position (b) to a third position (c). The movement of the indicator device 20 is directly proportional to the degree of deflection of the deflecting device 18, which is based on the degree of overflow of the embolization material 36. The degree of overflow of the embolization material 36 is correlated to the embolization pressure. Therefore, the indicia 23 may be correlated to embolization pressure and properly calibrated such that partial occlusion or full occlusion is indicated by a particular position. For example, in the present embodiment, position (a) may indicate the start of the occlusion, position (b) may indicate that occlusion is close to completion, and position (c) may indicate that full occlusion is completed. Accordingly, the indicator device 20, by its movement, gives an indication of the status of occlusion in the body vessel 100.

Alternatively, the condition of the occlusion may be determined based on the changed shape of the deflecting device 18 without using an indicator device 20. The deflecting device 18 may include a radiopaque material such that the changed shape of the deflecting device 18 during embolization may be observed by an external imaging device (not shown) through radiological intervention.

Alternatively, the changed shape of the deflecting device 18 may be observed by feeling the bulging area D of the vessel wall if the target site is close to the skin. The outside diameter of the deflecting device 18 in the expanded state is slightly larger than the diameter of the interior wall of the body vessel such that the deflecting device 18, in an expanded state, bulges the body vessel walls outwardly. When the deflecting device 18 is deflected by the embolization material 36 into a funnel shape, the contact area C between the deflecting device 18 and the interior wall 102 of the body vessel 100 is reduced. The bulging area D of the vessel walls is also reduced. Therefore, the changed bulging area of the body vessel wall may provide a tactile indication of the condition of occlusion.

Figure 9:
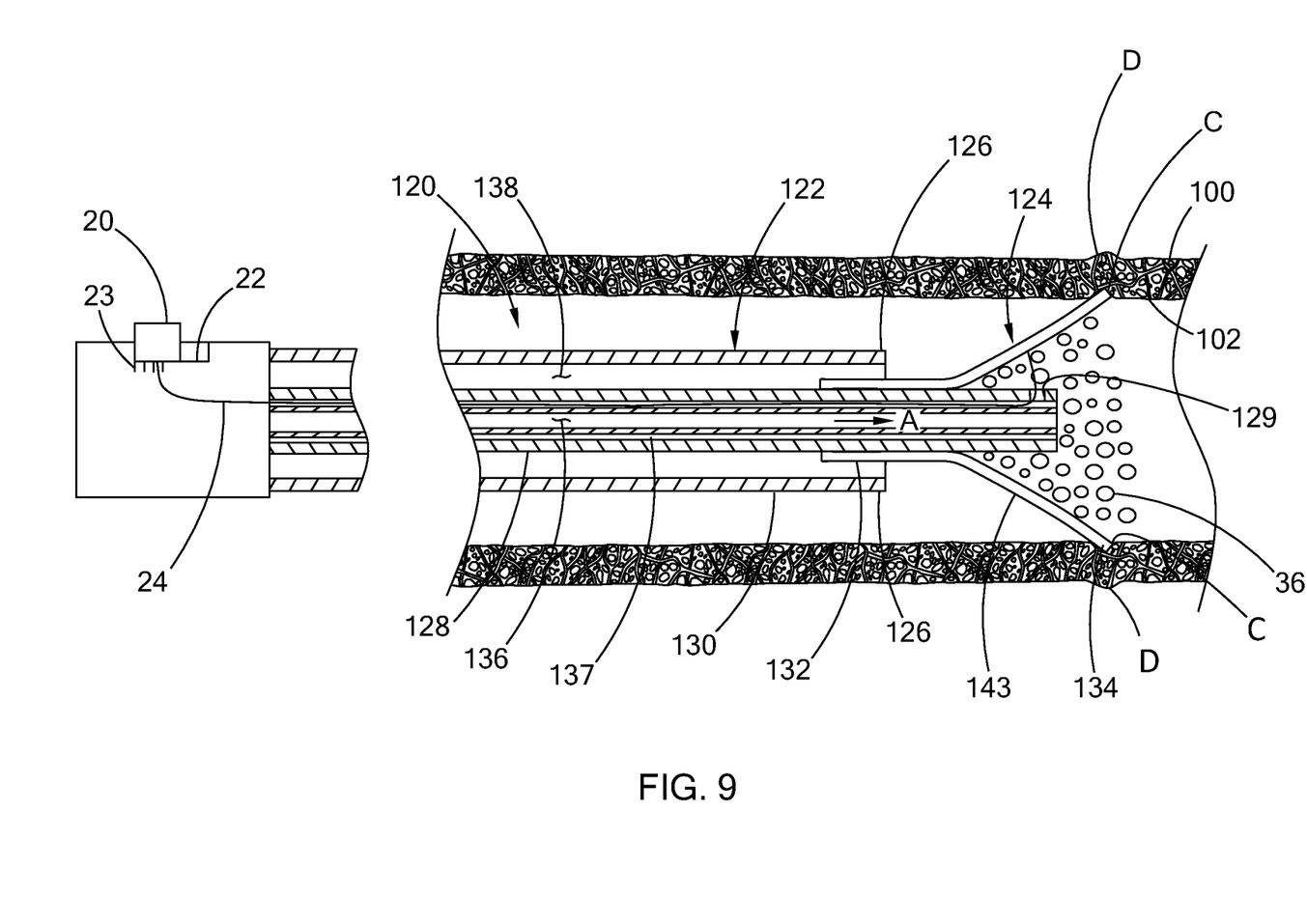
FIG. 9 is a partial, cross-sectional environmental view of a vascular occlusion device in a blood vessel in accordance with a second embodiment of the present disclosure.
Figure 10:
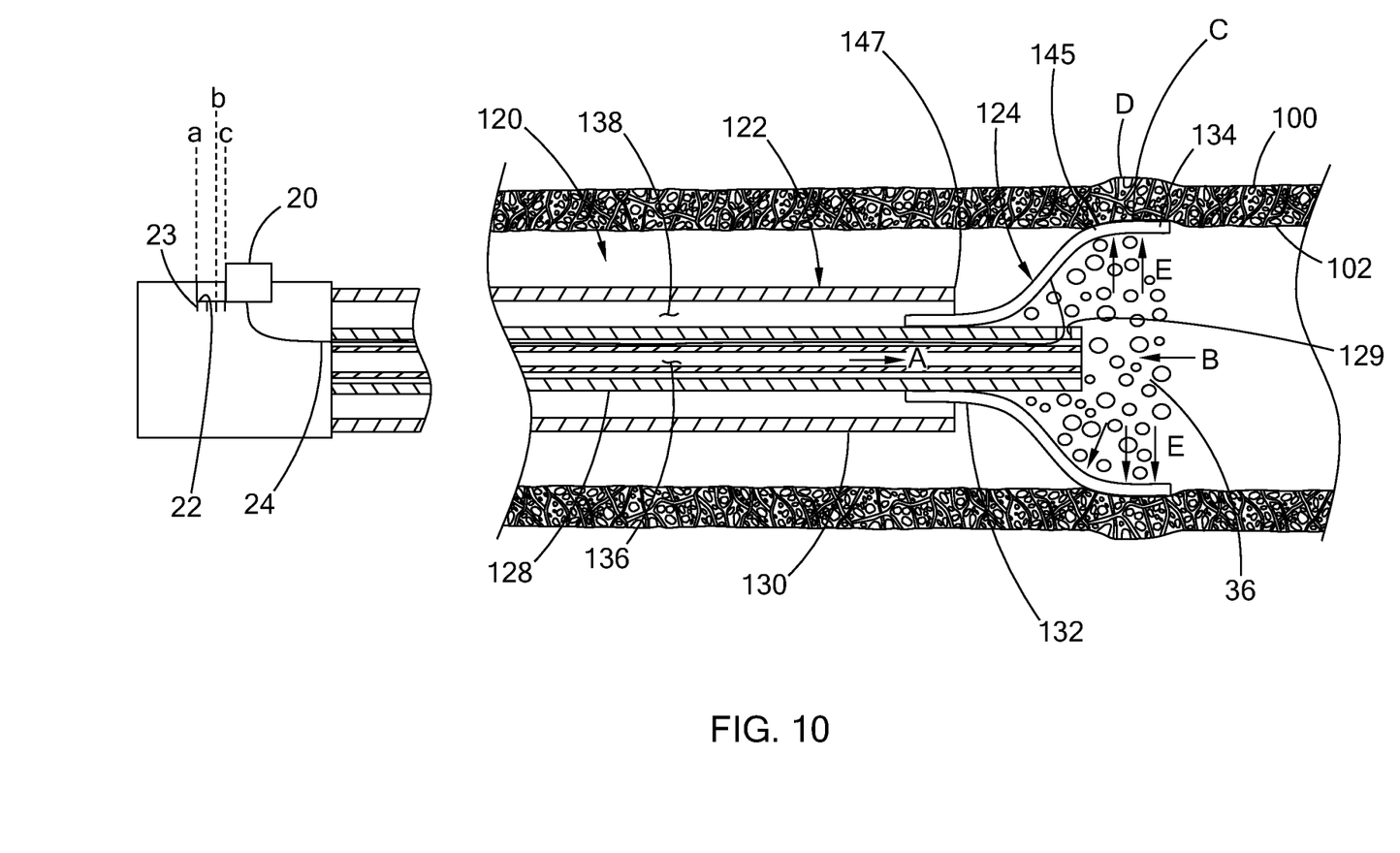
FIG. 10 is a partial, cross-sectional environmental view of the vascular occlusion device of FIG. 9, wherein an embolization material deflects the deflecting device into a funnel shape.

Referring to FIGS. 9 and 10, a vascular occlusion device 120 in accordance with a second embodiment of the present disclosure is structurally similar to the vascular occlusion device 62 of FIGS. 3 to 8, differing in the structure of the deflecting device. More specifically, the vascular occlusion device 120 includes an elongate member 122, a deflecting device 124, an indicator device 20, and a connecting member 24 connecting the deflecting device 124 to the indicator device 20. The elongate member 122 defines a distal end 126 and includes an inner tubular member 128 and an outer tubular member 130 coaxially disposed around the inner tubular member 128. The deflecting device 124 includes a proximal end 132 and a distal end 134. The proximal end 132 of the deflecting device 124 is placed adjacent to the distal end 126 of the elongate member 122. The distal end 134 of the deflecting device 124 is located distally from the distal end 126 of the elongate member 122. The deflecting device 124 is generally a covered stent and includes a plurality of struts 143 and a tubular portion 144. The tubular portion 144 is attached to the plurality of struts 143 and disposed between the proximal end 132 and the distal end 134 of the deflecting device 124. The tubular portion 144 may include graft materials and covers the openings defined between adjacent ones of the struts 143 to prevent blood and embolization material from flowing backward and through the deflecting device 124. The inner tubular member 128 defines an occlusion lumen 136 through which embolization material 36 is delivered into the body vessel 100 and a communication lumen 137. The connecting member 24 is disposed in the communication lumen 137. The inner tubular member 128 defines a radial opening 129 open to the communication lumen 137. A deployment lumen 138 is defined between the inner tubular member 128 and the outer tubular member 130 to receive the deflecting device 124 therein when the deflecting device 124 is in a collapsed state.

When the vascular occlusion device 120 is positioned at the target site, the deflecting device 124 is pushed outside the elongate member 122 and is expanded automatically into the expanded state. When the deflecting device 124 is deployed within the body vessel 100, the distal end 134 of the deflecting device 124 engages the interior walls 102 of the body vessel 100 to maintain the deflecting device 124 in place.

The plurality of struts 143 of the deflecting device 124 may be formed by nitinol and are configured to have a bell shape or a tapered shape in the expanded state. The proximal end 132 of the deflecting device 124 may be disposed within the outer tubular member 130 and outside the inner tubular member 132. The deflecting device 124, in the expanded state, blocks blood flow and additionally guides the embolization material to the target site. With the tapered shape of the tubular portion 144, the deflecting device 124 can be easily pulled into the outer tubular member 130 upon completion of embolization.

Referring to FIG. 10, after the deflecting device 124 is deployed in the body vessel 100, embolization material 36 is injected into the target site through the occlusion lumen 136 of the vascular occlusion device 120. As the body vessel 100 becomes occluded, the injected embolization material 36 is forced to flow backward toward the elongate member 122 and the deflecting device 124. The embolization material 36, which flows in the reversed direction B, starts to push and deflects the deflecting device 124 radially as indicated by arrow E into a funnel shape. The contact area C between the deflecting device 124 and the vessel wall 102 of the body vessel 100 is increased, thereby increasing the bulging area D of the body vessel 100. The funnel shape includes a wide portion 145 at the distal ends 134 and a narrow portion 147 at the proximal ends 132. A portion of the connecting member 24 is pulled outside the inner tubular member 128, causing the indicator device 20 to move distally from position (a) to position (c) or somewhere between position (a) and (c). The indicator device 20, by its movement, gives an indication of the condition of occlusion in the body cavity 100.

Alternatively, the deflecting device 124 may include a radiopaque material so that the deflection of the deflecting device 124 may be visually observed through radiological intervention. When the body vessel 100 is located adjacent to the skin, the changed bulging area D of the body vessel 100 may provide a tactile feedback of the condition of occlusion.

Figure 11:
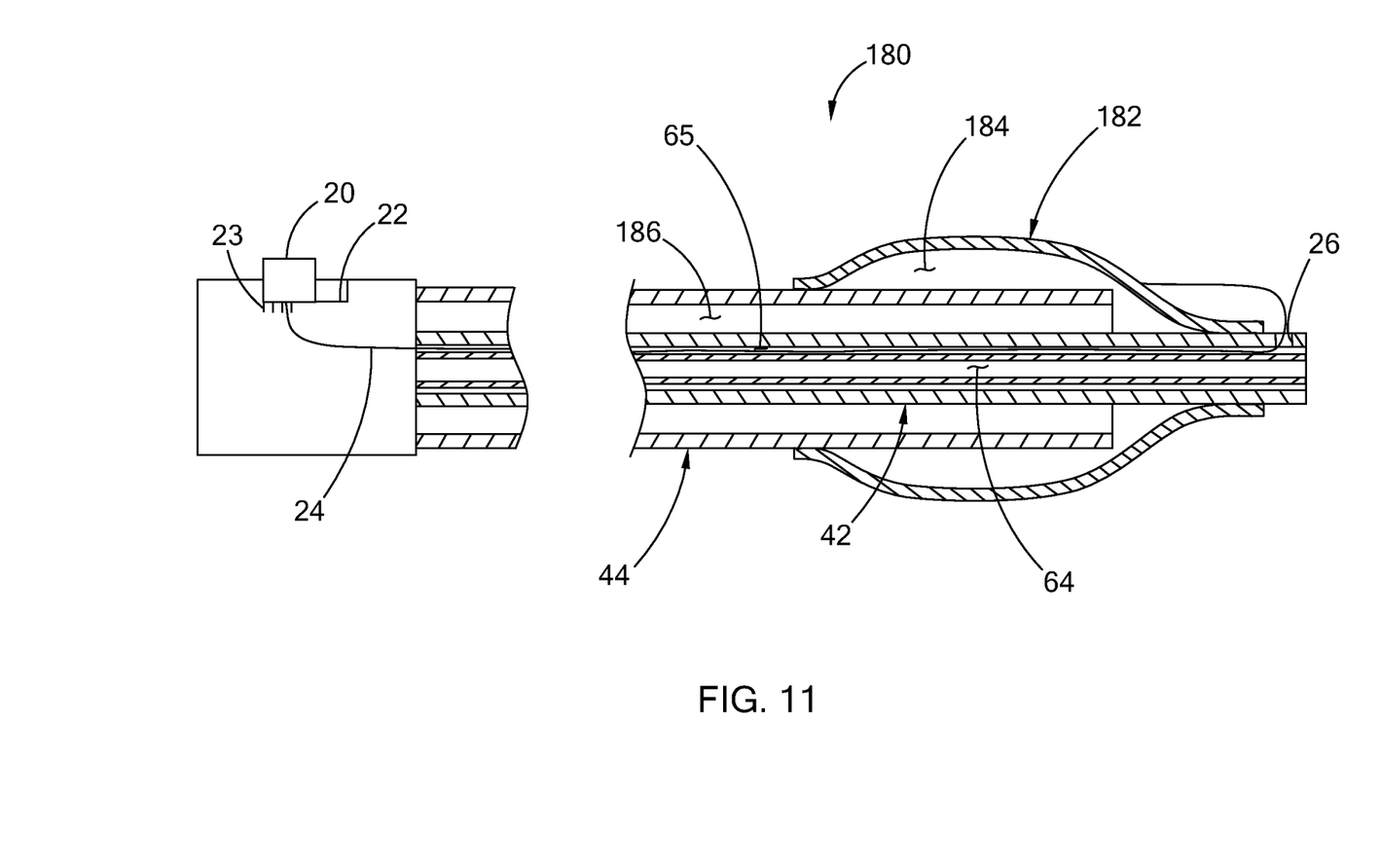
FIG. 11 is a partial, cross-sectional environmental view of a vascular occlusion device in accordance with a third embodiment of the present disclosure.

Referring to FIG. 11, a vascular occlusion device 180 in accordance with a third embodiment of the present disclosure is structurally similar to the vascular occlusion devices 62 and 120 of FIGS. 1 to 10, differing in the structure of the deflecting device 182. In the present embodiment, the deflecting device 182 is in the form of a non-self-expandable balloon and defines an interior space 184 in fluid communication with an inflation lumen 186 between the inner tubular member 42 and the outer tubular member 44. Similarly, the inner tubular member 42 defines an occlusion lumen 64 for injecting the embolization material 36 and a communication lumen 65 for receiving the connecting member 24. The connecting member 24 connects the indicator device 20 to the deflecting device 182 outside the inner tubular member 42 through the radial opening 26.

After the vascular occlusion device 180 is guided by the catheter to a target site, an inflation fluid, which may be any biocompatible fluid, may be injected through the inflation lumen 186 into the interior space 184 of the deflecting device 182 to inflate the deflecting device 182. Thereafter, embolization material is injected into the body cavity. As more embolization material is injected and the body cavity becomes occluded, the embolization material starts to overflow to push and deform the deflecting device 182. The deformed deflecting device 182 pulls the connecting member 24, which in turn pulls the indicator device 20 to move distally. Therefore, the indicator device 20 gives an indication of the condition of occlusion in the body cavity. Similarly, the deformation of the deflecting device 182 may be observed by radiological intervention.

It is to be understood that the embolization kit 60 described above is merely exemplary and that other kits, assemblies, and systems may be used to deploy any embodiment of the embolization particles without falling beyond the scope or spirit of the present invention. For example, a vascular occlusion device having multiple lumens may be used, wherein a first lumen is used to advance the embolization particles, a second lumen allows the vascular occlusion device to be advanced along a guide wire to a desired point of occlusion, and a third lumen allows for passage of the connecting member 24.

Figure 12:
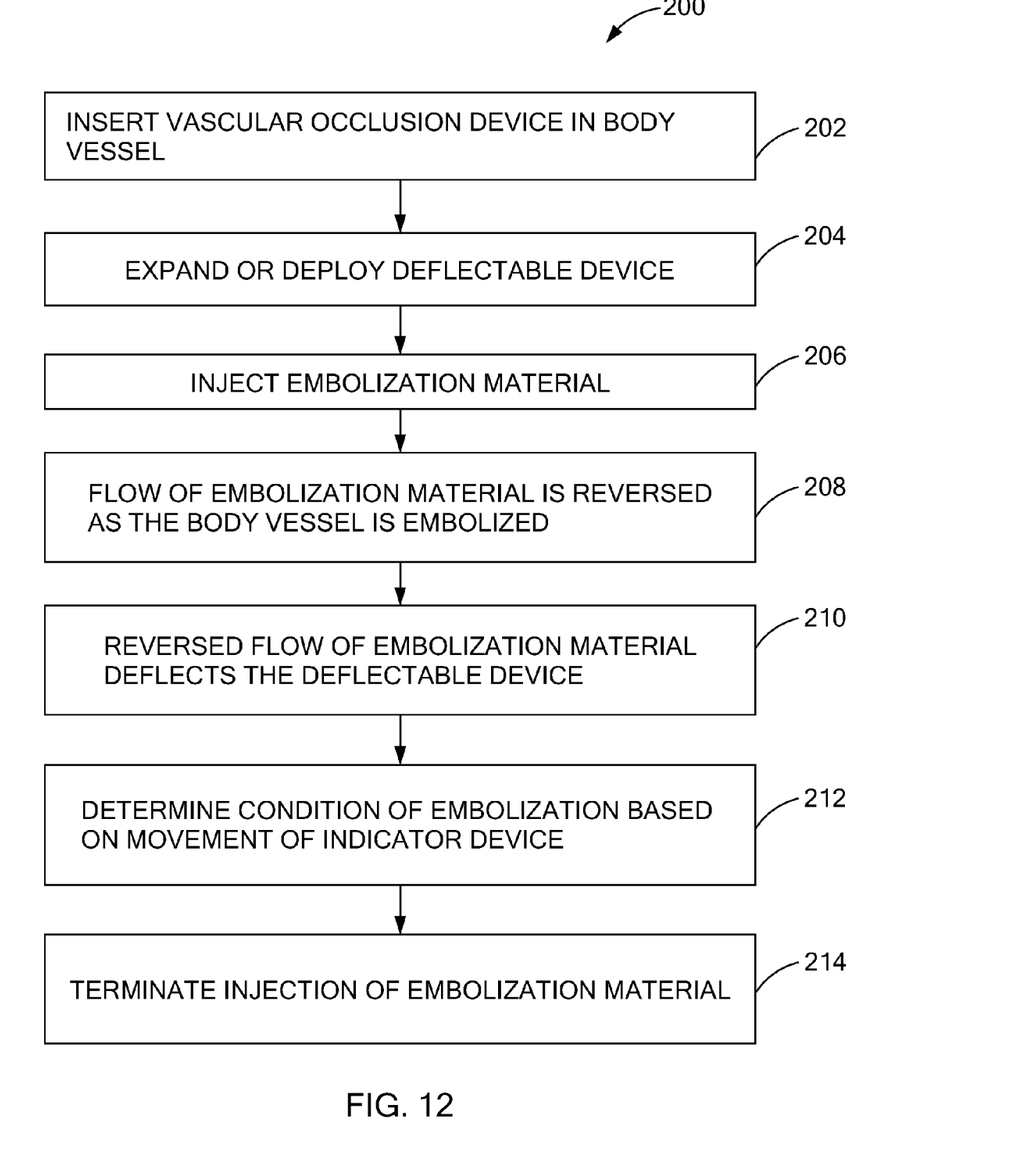
FIG. 12 is a flowchart illustrating a method of occluding a body cavity in accordance with the teachings of the present disclosure.

Referring to FIG. 12, a method 200 of occluding a body cavity in accordance with the teachings of the present disclosure is described. The vascular occlusion device 62 is inserted in a body vessel 100 in step 202. The deflecting device 18, 124 or 180 is expanded or inflated and deployed in the body vessel 100 after the distal end of the vascular occlusion device 18, 124 or 180 is positioned at the target site of the body vessel 100 in step 204. Embolization material 36 is injected into the body vessel 100 in step 206. The injection pressure increases as more embolization material is injected. When the body vessel 100 becomes occluded, the injected embolization material 36 starts to flow in a reverse direction toward the deflecting device 18, 124 or 180 in step 208. The deflecting device 18, 124 or 180 is deflected by the injected embolization material 36 in step 210. The deflection of the deflecting device causes the indicator device 20 to move distally. The clinician then determines the condition of embolization based on movement of the indicator device 20 in step 212. The clinician then terminates injection of the embolization material 36 to complete the embolization procedure in step 214.

It is understood that the assembly described above is merely one example of an assembly that may be used to deploy the occlusion device in a body vessel. Of course, other apparatus, assemblies and systems may be used to deploy any embodiment of the occlusion device without falling beyond the scope of the following claims.

The invention claimed is:

1. A vascular occlusion device for occluding a body cavity comprising:
an elongate member including a proximal end and a distal end, the elongate member being configured for injecting an embolization material into the body cavity through the distal end;
a deflecting device disposed at the distal end of the elongate member and configured to be deflected by the embolization material; and
an indicator device disposed at the proximal end of the elongate member, wherein the indicator device indicates a status of occlusion of the body cavity based on deflection of the deflecting device by the embolization material; and
a connecting member connecting the deflecting device to the indicator device;
wherein when the deflecting device is deflected radially inward by the embolization material, the deflecting device pulls the connecting member and the connecting member pulls the indicator device to move distally.

2. The vascular occlusion device of claim 1, wherein the deflection of the deflecting device causes the indicator device to move.

3. The vascular occlusion device of claim 1, wherein the connecting member is a wire.

4. The occlusion device of claim 1, wherein the deflecting device includes a plurality of struts and a tubular portion covering the plurality of struts.

5. The vascular occlusion device of claim 4, wherein the plurality of struts are pivotably secured to the distal end of the elongate member.

6. The vascular occlusion device of claim 1, wherein the elongate member includes an inner tubular member and an outer tubular member surrounding the inner tubular member to define a deployment lumen therebetween, the inner tubular member protruding distally from the outer tubular member.

7. The vascular occlusion device of claim 6, wherein the inner tubular member defines an occlusion lumen through which the embolization material is injected and a communication lumen for receiving a connecting member.

8. The vascular occlusion device of claim 7, wherein the inner tubular member defines a radial opening open to the communication lumen.

9. The vascular occlusion device of claim 6, wherein the deflecting device is attached to the inner tubular member.

10. The vascular occlusion device of claim 6, wherein the deflecting device is received in the deployment lumen when the deflecting device is in a collapsed state.

11. The vascular occlusion device of claim 1, wherein the deflecting device is a balloon.

12. The vascular occlusion device of claim 1, wherein the embolization material deflects the deflecting device when the embolization material overflows.

13. A vascular occlusion device for occluding a body cavity, comprising:
an inner tubular member defining an occlusion lumen and a communication lumen, the elongate member being configured for injecting an embolization material into the body cavity in a first direction through the occlusion lumen;
an outer tubular member surrounding the inner tubular member to define a deployment lumen therebetween;
a deflecting device selected from one of a covered stent and a balloon and attached to a distal end of the inner tubular member;
an indicator device provided at a proximal end of the inner tubular member; and
a connecting member extending in the communication lumen and connecting the deflecting device to the indicator device,
wherein when the embolization material overflows, the embolization material deflects the deflecting device radially inward, thereby causing the indicator device to move distally.

* * * * *